United States Patent [19]

Collins

[11] Patent Number: 4,477,391

[45] Date of Patent: Oct. 16, 1984

[54] AMINO ACID ISOMERS, THEIR PRODUCTION AND THEIR MEDICINAL USE

[76] Inventor: James F. Collins, Flat 7, Langwood, 87 Langley Rd., Watford, Hertfordshire, England

[21] Appl. No.: 356,036

[22] Filed: Mar. 8, 1982

[30] Foreign Application Priority Data

Aug. 14, 1981 [GB] United Kingdom ............... 8124899

[51] Int. Cl.$^3$ .............................................. C07F 9/38
[52] U.S. Cl. .............................. 260/502.5 G; 548/253; 260/502.3; 260/513 N; 260/961; 260/970; 424/185; 424/211; 424/269; 424/311; 424/314; 424/315
[58] Field of Search ................ 260/502.5 G, 970, 961

[56] References Cited

U.S. PATENT DOCUMENTS 2,934,561  4/1960  Rogers ........................... 260/501.12
4,168,963  9/1979  Rupp et al. ................... 260/502.5 G

OTHER PUBLICATIONS

Abramov et al., "J. Gen. Chem. U.S.S.R.", vol. 22 (English Translation), pp. 309-313, Jan.-Mar. 1952.
Kosolapoff, "Organophosphorus Compounds", 1950, pp. 121-125.

*Primary Examiner*—J. E. Evans
*Attorney, Agent, or Firm*—Cushman, Darby & Cushman

[57] ABSTRACT

The (−)-D-isomers of compounds of the general formula

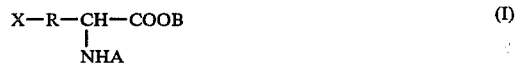

in which
X stands for an acidic radical, especially a radical of phosphonic acid, sulphonic acid, boronic acid or tetrazole,
R stands for an alkylene, alkenylene or alkynylene radical with 3 or more carbon atoms, preferably 3 to 6 carbon atoms, or a $C_3$ to $C_7$ cycloalkyl radical, and
A and B independently of each other stand for a hydrogen atom or a lipophilic radical, especially an ester radical, or salts thereof, or pharmaceutically acceptable bioprecursors thereof, especially (−)-D-aminophosphonopentanoic acid and (−)-D-aminophosphonoheptanoic acid, find use in the treatment of diseases of the central nervous system.

The compound aminophosphonoheptanoic acid is also novel as a racemic mixture and the present invention also relates to that compound in racemic form which may be used in the same way as the said (−)-D-isomers.

12 Claims, No Drawings

AMINO ACID ISOMERS, THEIR PRODUCTION AND THEIR MEDICINAL USE

The present invention relates to certain new isomers which have use in the treatment of diseases of the central nervous system and to processes for their production.

The compounds of the invention can be administered by intracerebral injection. While this would be a means of administration of last resort in therapy, it has particular significance in research into diseases of the central nervous system. There is much interest currently in developing an understanding of the action of certain compounds produced by the body on the central nervous system (CNS) of vertebrate mammals. Certain receptors in the CNS are excited by amino acids or derivatives thereof. These excitors cause neuronal degeneration and are believed to be responsible for example for Huntington's Chorea disease. Current research is directed at identifying antagonists which block the receptors against excitors. A problem, however, is in determining which receptors are blocked by which antagonists. We have now surprisingly found that (—)-D-amino phosphoroheptanoic acid is a blocker of isotenic acid-excited receptors but not a blocker of Kainic acid-excited receptors. This compound is therefore of great value in CNS research as a means of blocking ibotenic acid-excited receptors while leaving Kainic acid-excited receptors free to be acted on by candidate antagonists.

According to the present invention we provide, as new compounds, the (—)-D-isomers of compounds of the general formula

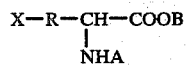 (I)

in which
X stands for an acidic radical, especially a radical of phosphonic acid, sulphonic acid, boronic acid or tetrazole,
R stands for an alkylene, alkenylene or alkynylene radical with 3 or more carbon atoms, preferably with 3 to 6 carbon atoms, or a $C_3$ to $C_7$ cycloalkyl radical, and A and B independently of each other stand for a hydrogen atom or a lipophilic radical, especially an ester radical,
or salts thereof, or pharmaceutically acceptable bioprecursors thereof.

Among the preferred isomers of the present invention are those in which X stands for a radical of phosphonic acid, A and B stand for hydrogen atoms and R either stands for a propyl or pentyl radical, i.e. (—)-D-aminophosphonopentanoic acid and (—)-D-aminophosphonoheptanoic acid.

The compound aminophosphonoheptanoic acid is also novel as a racemic mixture and the present invention also relates to that compound in racemic form.

For the purposes of this specification the term 'pharmaceutically acceptable bioprecursor' of an active compound of the invention means a compound having a structural formula different from the active compound but which nonetheless, upon administration to an animal or human being is converted in the patient's body to the active compound.

The present invention further relates to processes for the production of compounds of the present invention, in which:
(a) if a compound of formula (I) in which X stands for a phosphonic acid radical is required,
a dibromo compound of the general formula

 (II)

in which, R has the above-mentioned meaning, is reacted with a compound of the general formula

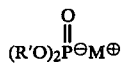 (III)

in which,
R' stands for an alkyl group, preferably an ethyl group,
$M^\oplus$ stands for an alkali metal carbon, preferably a sodium cation,
and the resulting compound of the general formula

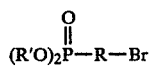 (IV)

is heated, preferably in ethanol, with diethyl acetamidomalonate and the resulting condensation product of the general formula

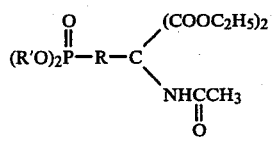 (V)

is subjected to decarboxylation, preferably in boiling hydrochloric acid, or, especially, using iodotrimethyl silane, to give a compound according to the present invention of the general formula

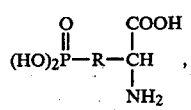 (Ia)

or
(b) if a compound of formula (I) in which X stands for a sulphonic acid radical is required,
a compound of the general formula

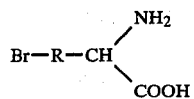 (VI)

in which R has the abovementioned meaning, is reacted with sodium sulphide, to give a compound of the general formula

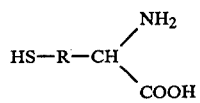 (VII)

which is then heated to give a compound of the general formula

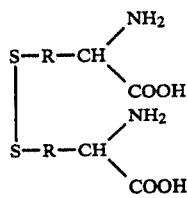 (VIII)

which then is reacted with bromine to give a compound according to the present invention of the general formula

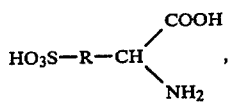 (Ib)

(c) if a compound of formula (I) in which X stands for a triazolyl radical is required,
a compound of the general formula

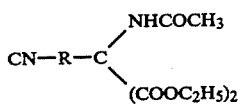 (IX)

is reacted with sodium azide to give a compound according to the present invention of the general formula

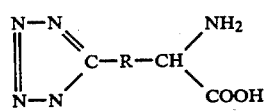 (Ic)

(d) if a compound of formula (I) in which X stands for a boronic acid radical is required,
a compound of the general formula MgBr—R—Br  (X)

in which R has the abovementioned meaning, is reacted with a trialkyl borate, especially triethyl borate, of the general formula (R'O)$_3$B  (XI)

in which R' represents an alkyl group, to give a compound of the general formula (R'O)$_2$B—R—Br  (XII)

which is then reacted with a diethylacetamidomalonate and the product of the general formula

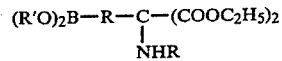 (XIII)

is then hydrolysed to give a compound according to the present invention of the general formula

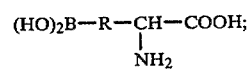 (Id)

and the product of reaction variant (a), (b), (c) or (d) of formula (Ia), (Ib), (Ic) or (Id), respectively is, before or after separation of the (−)-D-isomer, converted, if desired into a corresponding compound in which the amino group or carboxylic acid group carries lipophilic group and/or converted into a salt thereof.

Among the new salts of the isomers of the present invention, those salts that are pharmaceutically acceptable are particularly important and are preferred.

The new free isomers of the general formula (I) and their salts can be interconverted in any suitable manner; methods for such interconversion are known in the art.

The separation of the (−)-D-isomer may be carried out by generally known methods, such as reacting the racemic mixture with an optically active base and separating out the salts formed. An appropriate method of separation has been found to be reacting the racemic mixture produced by a process of the invention with L-lysine, thereby forming diastereomers, separating the salt containing the (−)-D-isomer by crystallisation, followed by decomposition of the salt to obtain the (−)-D-isomer.

The starting compounds used in the process variants according to the present invention are known compounds or can be produced by processes similar to those used for the production of such known compounds.

All the process variants are preferably carried out in the presence of an inert organic solvent as the diluent. It is preferred that the reactions are carried out at the boiling point of the solvent used, that is to say, at reflux temperature.

The following reaction schemes illustrate the processes according to the present invention:

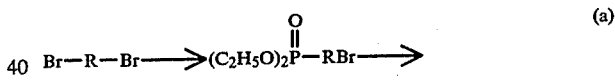 (a)

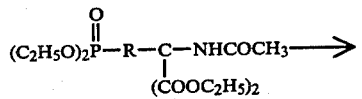

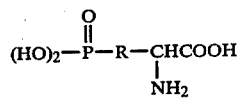

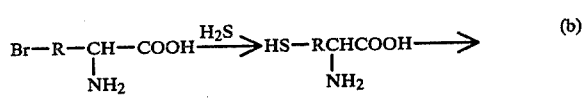 (b)

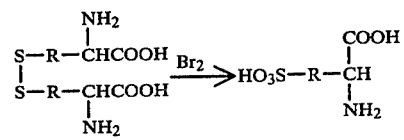

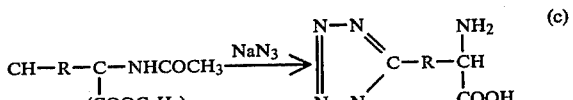 (c)

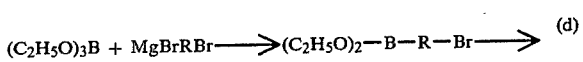 (d)

-continued

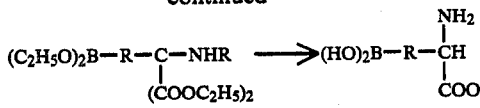

The isomers of the present invention have use in the treatment of diseases of the central nervous system, particularly Alzheimer's disease and also Huntingtons disease and certain forms of epilepsy. Those isomers which comprise lipophilic radicals may be applied by conventional pharmaceutical administration routes such as parenteral administration, e.g. intravenous administration.

The following Example illustrates a process for the production of an isomer of the present invention.

EXAMPLE (a) Synthesis of (−)2-amino-7-phosphonoheptanoic acid 1,5-dibromopentane→diethyl-5-bromopantane phosphonate

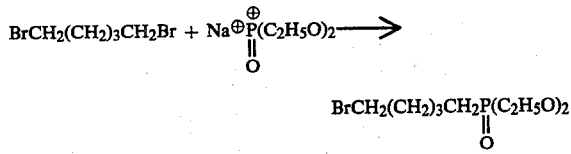

Diethyl phosphite was dissolved in anhydrous diethyl ether, and an equimolar quantity of sodium added in small pieces over a period of ½ hr; hydrogen being given off during this reaction. Four mole equivalents of 1,5-dibromopentane were dissolved in anhydrous diethyl ether, and the sodium salt of diethyl phosphite added, as a suspension, with stirring. The mixture was stirred for 36 hours, then refluxed for 2 hours, during this process, the fine precipitate of NaBr flocculated, and was filtered off. The ether was evaporated off to leave a colourless liquid. Excess dibromopentane was distilled off at 1 mm Hg, to leave a colourless oil which was taken up in 50/50 pet. ether/ether and columned on Kieselgel 60 in 50/50 pet. ether/ether. The first fraction contained unreacted diethyl phosphite; the product came off in pure diethyl ether.

(b) Diethyl-5-bromopentane phosphonate→acetamido adduct

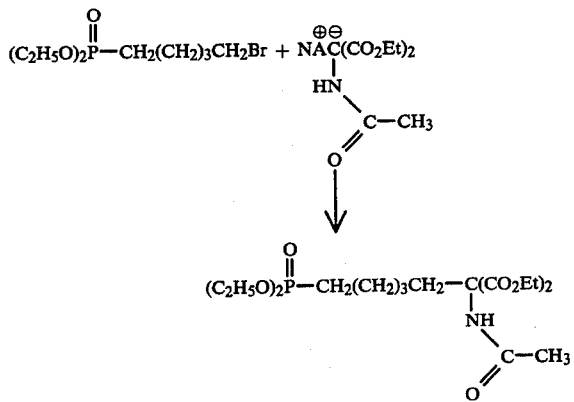

The sodium salt of diethyl acetamidomalonate, was prepared by dissolving sodium in a slight excess of ethyl alcohol, and adding an equimolar quantity of diethyl acetamido malonate. The mixture was refluxed until a brown colouration indicated the formation of the sodium salt. The ethyl alcohol was evaporated off at 80° C., in vacuo, to leave a ten syrup; the remaining alcohol was removed by successive distillations with dry toluene, to leave a tan solid. The sodium salt was suspended in dry toluene, and diethyl carbonate added, the diethyl-5-bromopentane phosphonate was added, and the mixture refluxed for 3 days. The resulting NaBr was filtered off, and the solvents evaporated to leave a sticky, dark brown syrup. This was taken up in diethyl ether and columned on Kieselgel 60. Unreacted sodium diethyl acetamido malonate, and diethyl-5-bromopentane phosphonate, came off with diethyl ether, and were separated by crystallisation of sodium diethyl acetamido malonate from ether solution. The product was eluted off the column with chloroform, as a light yellow viscous syrup.

(c) Acetamido adduct→(±)2-amino-7-phosphonoheptanoic acid

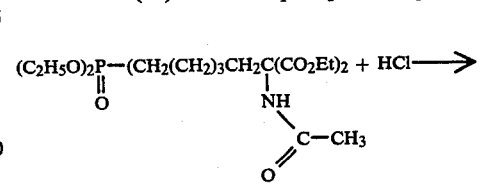

The acetamido adduct was refluxed together with 6MHCl overnight; the solution was evaporated to dryness, and the solid taken up in 5% aqueous ethanol. The free acid was precipitated by careful addition of propylene oxide and filtered off. The acid was dissolved in water and passed down on "Dowex" 50×8 (H+) column. The acid was washed with 5 bed volumes of water followed by elution with 2M aqueous pyridine. The amino acid containing fractions were avaporated to dryness, and the product recrystallised from water/ethanol.

(d) Resolution of 2-amino-7-phosphonoheptanoic acid

Equimolar quantities of the phosphonic acid, and L-lysine, were dissolved in water and warmed for ½ hr at 60° C. Two volumes of hot methanol were then added and the mixture brought to room temperature. Diethyl ether was added carefully, until a slight cloudiness appeared in the solution, which was left to stand. The phosphonic acid/lysine salt was filtered off and dissolved in water. A "Dowex" 50×8 column was prepared by passed 2M pyridine down it, and washing with water, the lysine salt solution was passed down the column and washed through with water, the phosphonic acid passing straight through. The amine acid containing fractions were collected and evaporated to dryness; a solution of known concentration was then made up, and the rotation of plane polarised light recorded on a "TBL" Automatic Polarimeter 143D using a mercury lamp. The first isomer to be precipitated was found to be (−), and circular dichroism studies indicated it to have the D configuration.

What is claimed is:

1. A process for the production of a compound of formula (I)

$$X-R-\underset{\underset{NHA}{|}}{CH}-COOB \quad (I)$$

X stands for a phosphonic acid radical,
R stands for an alkylene, alkenylene, or alkynylene radical with 3 or more carbon atoms, or a $C_3$ to $C_7$ cycloalkyl radical, and
A and B independently of each other stand for a hydrogen atom or an ester group, or a salt thereof comprising reacting (a) a dibromo compound of the formula $$Br-R-Br \quad (II)$$

with a compound of the formula $$\underset{\underset{(R'O)_2P^\ominus M^\oplus}{\|}}{O} \quad (III)$$

R' stands for an alkyl group,
M⊕ stands for an alkali metal cation, and heating the resulting compound of the general formula $$\underset{\underset{(R'O)_2P-R-Br}{\|}}{O} \quad (IV)$$

with diethyl acetamidomalonate, and subjecting the resulting condensation product of the formula $$(R'O)_2\underset{\|}{\overset{O}{P}}-R-\underset{\underset{\underset{O}{\|}}{NHC-CH_3}}{\overset{(COOC_2H_5)_2}{C}} \quad (V)$$

to decarboxylation to give a compound of the formula $$(HO)_2\underset{\|}{\overset{O}{P}}-R-\underset{\underset{NH_2}{|}}{\overset{COOH}{CH}}. \quad (Ia)$$

2. A process according to claim 1 wherein R' is ethyl and M⊕ is a sodium cation.

3. A process according to claim 2 wherein compound (IV) is heated in ethanol.

4. A process according to claim 2 wherein compound (V) is decarboxylated in boiling hydrochloric acid.

5. A process according to claim 2 wherein compound (V) is decarboxylated with iodotrimethyl silane.

6. A process according to claim 5 wherein compound (IV) is heated in ethanol.

7. A process according to claim 2 in which the (−)-D-isomer is separated by reacting the final product with an optically active base and separating out the salts formed.

8. A process according to claim 7 in which the optically active base is L-lysine and the process includes the steps of separating the salt of the (−)-D-isomer by crystallization followed by decomposition of said salt to obtain the (−)-D-isomer.

9. A process according to claim 1 wherein the (−)-D-isomer is separated by recycling the product of reaction (a) with an optically active base and separating out the salts formed.

10. A process according to claim 9 wherein the (−)-D-isomer is separated by reacting the product of reaction (a) with L-lysine, thereby forming diastereomer salts, separating the salt containing the (−)-D-isomer by crystallisation, followed by decomposition of the said salt to obtain the (−)-D-isomer.

11. A process according to claim 1 wherein R is an n-pentyl radical and A and B are hydrogen atoms.

12. A process according to claim 1 including the step of converting at least one of an amino group or a carboxylic acid group carrying an ester group to a salt thereof.

* * * * *

UNITED STATES PATENT AND TRADEMARK OFFICE
CERTIFICATE OF CORRECTION

PATENT NO. : 4,477,391
DATED : October 16, 1984
INVENTOR(S) : COLLINS, James; CURRY, Kenneth; and SCHWARCZ, Robert It is certified that error appears in the above-identified patent and that said Letters Patent is hereby corrected as shown below:

On the title page;

[76] Inventors:

The second and third inventors names were omitted and should read as follows:

-- Kenneth Curry, University of British Columbia, Department of Physiology, Vancouver B.C. Canada and Robert Schwarcz, 6719 Bonnie Bridge Drive, Apartment 202, Baltimore, Md. 21209 --

Signed and Sealed this

Ninth Day of July 1985

[SEAL]

Attest:

DONALD J. QUIGG

Attesting Officer    Acting Commissioner of Patents and Trademarks